United States Patent
Berestov

(10) Patent No.: US 6,381,302 B1
(45) Date of Patent: Apr. 30, 2002

(54) COMPUTER ASSISTED 2D ADJUSTMENT OF STEREO X-RAY IMAGES

(75) Inventor: Alexander Berestov, San Jose, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/610,579

(22) Filed: Jul. 5, 2000

(51) Int. Cl.⁷ .................................................. A61B 6/02
(52) U.S. Cl. .......................................... 378/41; 378/98
(58) Field of Search .......................... 378/41, 98, 98.2

(56) References Cited

U.S. PATENT DOCUMENTS

| | | | | |
|---|---|---|---|---|
| 4,669,048 A | * | 5/1987 | Ackermann et al. | 382/154 |
| 6,047,080 A | * | 4/2000 | Chen et al. | 382/128 |

OTHER PUBLICATIONS

Talukdar, A. et al.; Modeling and Optimization of Rotational C–Arm Steroscopic X–Ray Angiography, IEEE Transactions on Medical Imaging, vol. 18, No. 7, pp. 604–616, (Jul. 1999).

Woods, A. et al.; Image Distortions in Stereoscopic Video Systems, SPIE, vol. 1915 Stereoscopic Displays and Applications IV, pp. 36–48, (1993).

\* cited by examiner

*Primary Examiner*—David V. Bruce
(74) *Attorney, Agent, or Firm*—Fitzpatrick, Cella, Harper & Scinto

(57) ABSTRACT

A method locates one or more physical pointers around the body, such as a steel ball or other distinguishable item, and captures two distinct x-ray images (410) of the body, such that the physical pointers are captured in the x-ray images. The locations of the physical pointers in the images (410) are used to estimate the horizontal and vertical distortions. The images (410) are adjusted vertically and horizontally to correct for any estimated distortions. A disparity map may then be calculated manually or using the classic epipolar stereo matching technique. The disparity map provides the location of one or more distinctive objects inside the body.

12 Claims, 6 Drawing Sheets

(a)

(b)

COMPUTER ASSISTED 2D ADJUSTMENT OF STEREO X-RAY IMAGES

FIELD OF THE INVENTION

This invention pertains to the field of three-dimensional imaging and analysis. More specifically, the invention pertains to a system and method for adjusting stereo x-ray images to correct for any vertical or horizontal distortions.

BACKGROUND

For both real-world and computer-generated imaging applications, there is a growing need for display techniques that enable determination of relative spatial locations between objects in an image. Once the spatial relations are established, a user can move through the display space and manipulate objects easily and accurately.

Another related problem is object recognition and localization. One of the basic steps in computer object recognition is to collect as much information as possible about the object by analyzing the image. For example, the space structure of the object can give information that is important for many applications, such as three-dimensional object modeling, vehicle navigation, and geometric inspection. One of the more recent applications is in Computer Aided Diagnosis (CAD), which is a diagnosis made by radiologists utilizing a computer output as a "second opinion".

A final related problem is binocular stereo, which is the determination of the three-dimensional shape of visible surfaces in a static scene from images taken of the same scene by two cameras or one camera at two different positions. Application of the binocular stereo to X-ray imaging is not easy because there are no visible surfaces on the radiograph and information about different objects can be located at the same areas of the X-ray image. Nevertheless, some of the stereo methods used to analyze standard images could be applied to the analysis of radiograph pairs that were captured using two X-ray sources or by using other stereo imaging techniques.

The approaches used to analyze and resolve the problems described above when examining non-radiograph images can also be applied to radiograph images; provided, however, that the geometry of the stereo digital radiograph system is known. If this is the case, it would be possible to point to an object in the radiograph and calculate an exact location of this object within the radiographed body. It would also be possible to make a disparity map that graphically represents the distance from the X-ray source to every "visible" object in the image. This information could be very important in many medical applications such as surgery, therapy, and related medical applications.

It is straightforward and conventional wisdom that the stereo correspondence problem is a one-dimensional search problem. This is true if the epipolar constraint is known, or selected, from the beginning. In the general case, for example, calibration is used to recover the epipolar geometry accurately. The problem is that even if the imaging geometry is carefully arranged, there are often still errors in the system. This results in corresponding points that are not strictly on the same horizontal lines and distorted vertical positioning. There are other reasons the pixels in one X-ray image may not have matching pixels lying along the same row in the second image and even shifted horizontally. The two major problems result in keystone distortion, vertical parallax and shear distortion.

A well-known effect is keystone distortion (FIG. 2). Keystone distortion causes vertical parallax in the stereoscopic radiograph due to the baseline of the two X-ray sources being not parallel to the surface of the screen. This is also the case when the stereo radiographs are obtained by the rotation of the object. In one of the radiograph, the image of the square appears larger at one side than at the other. In the other radiograph, this effect is reversed. This results in a vertical difference between homologous points, which is called vertical parallax. The amount of vertical parallax is greatest in the corners of the image.

Another distortion appears when the base line between two X-ray sources and the bottom of the screen are not parallel to the horizon. When the stereo radiographs are obtained by the rotation of the object, this distortion appears when the axis of rotation is not vertical. This distortion also causes vertical parallax as well as shear distortion (FIG. 2), which influences the correct estimation horizontal location of homologous points.

Numerous algorithms for image matching have been proposed. They can roughly be classified into two categories. In the first category, the algorithms attempt to correlate the gray levels of image patches, assuming that the image patches present some similarity. In the second category, the algorithms first extract salient primitives or feature points from the images, such as edge segments or contours, and then match these features in two views. These methods are relatively fast, because only small subsets of the image pixels are used, but often fail because the chosen primitives cannot be reliably detected in the images.

What is needed is a system and method for quickly determining the geometry of a stereo digital radiograph system enabling quick and accurate correction of distortion in the radiographs such that objects in the radiograph can be located in three dimensional space.

DISCLOSURE OF INVENTION

The present system and method provide a means for quickly and accurately determining the geometry of a stereo x-ray imaging system, enabling the location of objects in the radiograph in three dimensional space. For the purposes of this description, a "body" is the primary item being radiographed. Traditionally, this is a patient at a medical hospital. An "object" is an item that is located within the body such as a bone or joint in the body. A "physical pointer" is an item that absorbs or reflects x-rays such that a mark or point is visibly evident in the radiograph when captured by a digital radiograph system.

The method begins by establishing an initial correspondence using one or more physical pointers around or inside the body. For example, the pointers could be steel balls that make a distinct white spot on the radiographs. Alternatively, other distinctive pointers could be used, for example objects within the body such as bones or joints.

Once the images (410) of the body are complete, the physical pointers are used to estimate the epipolar geometry and horizontal distortions of the radiographs. Depending on the distortion estimates, each radiograph is transformed by adjusting it vertically and horizontally. The classical epipolar stereo matching technique can then be used to calculate a disparity map of recognizable objects within the body. Finally, standard geometric properties can be used to calculate the three dimensional location of the objects inside the body.

DETAILED DESCRIPTION OF THE PREFERRED EMBODIMENTS

The present invention can be used in conjunction with any number of different radiograph imaging devices including x-ray machines and digital radiograph systems. The present specification describes the invention as being used in conjunction with digital radiograph systems, for illustration purposes only.

Figure 1:
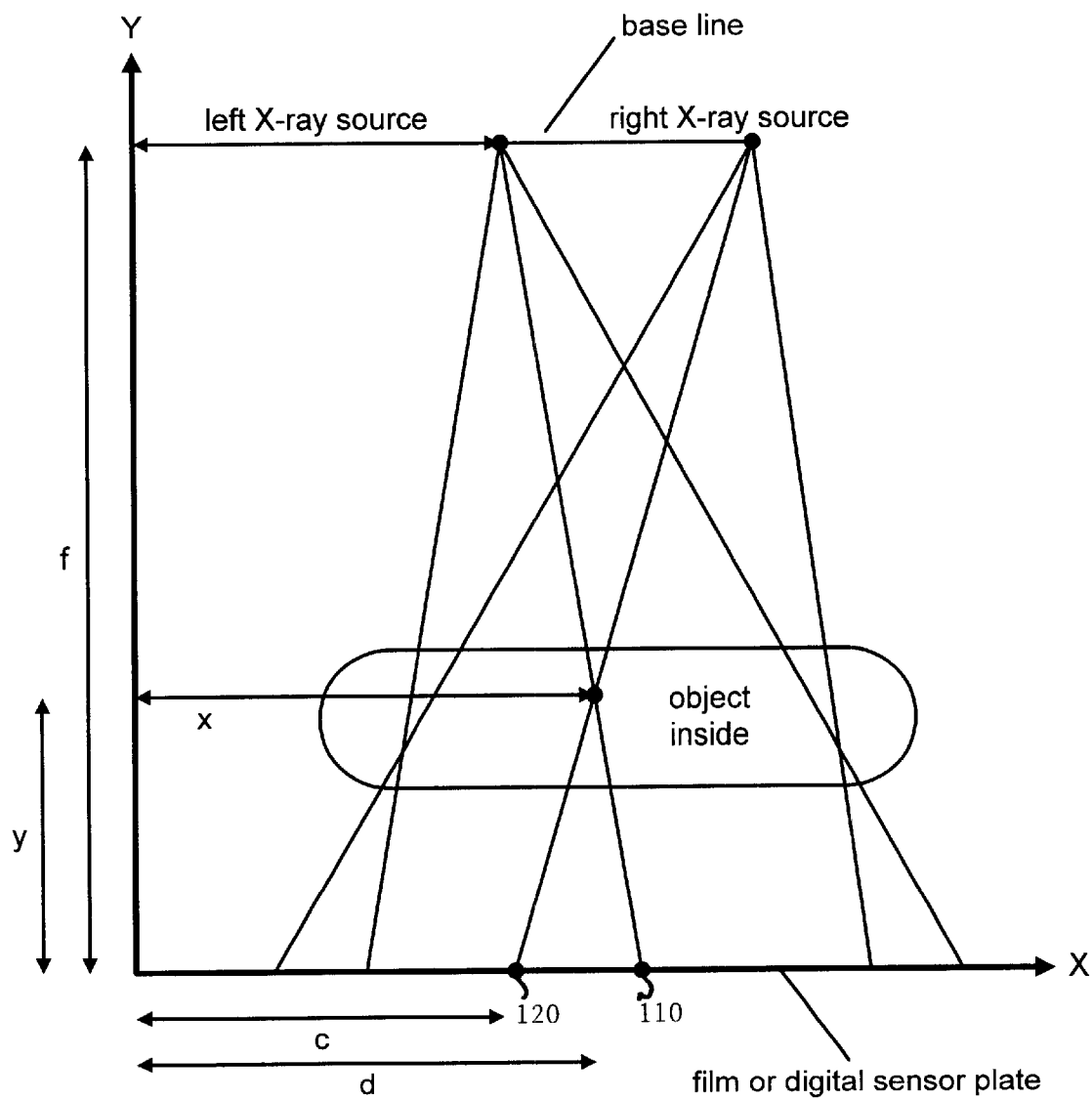
FIG. 1 is an illustration of the geometry of a conventional stereoscopic x-ray imaging system.

For the purposes of this description, a X-Y coordinate system will be used, where the Y-axis is perpendicular to the capture screen and the X-axis is parallel to the base line of the imagining device as shown in FIG. 1. In this description, the x and y origins are the coordinates of an object inside the body. Simple geometry of the system gives us the necessary relationships between parameters:

$$x = \frac{da + db - dc}{b + d - c}, \quad \text{(Equation 1)}$$

$$y = f\frac{d-c}{b+d+c}, \quad \text{(Equation 2)}$$

where f is the focal length, b is the distance between the location of the x-ray imaging device when taking a first image and taking a second image respectively (the base), a the X coordinate of the x-ray imaging device when capturing the first image, c is the X coordinate of the object in the first image and d is the X coordinate of the object in the first image.

In a first embodiment, a digital radiograph system is used to capture an x-ray of a body comprising one or more objects. When the x-ray is taken, however, the body is "flattened" from three dimensions to two dimensions, resulting in the loss of information, such as spatial size and the spatial relations between objects in the image. One way of replacing the lost information is to take two or more radiographs of the same bodies from different angles, and to extrapolate the spatial information accordingly. In order to combine the images properly, however, portions of the first image 110 must be corresponded to the relevant portions in the second image 120.

It is often assumed that the stereo image correspondence problem is a one dimensional search problem. This is true if the spatial relationships between the locations from which the images were taken, called the epipolar geometry, is known from the beginning. In the classical method, known as the calibrated route, both cameras (or viewpoints) are calibrated with respect to some world coordinate system. That information is then used to calculate the epipolar geometry by extracting the essential matrix of the system. The three-dimensional Euclidean structure of the imaged scene can then be computed.

If the two cameras are not carefully placed or the angles used to capture the images result in keystone distortion or vertical parallax, however, recovery of the epipolar geometry is necessary. In the ideal case, the epipolar lines of the two images are horizontal. In order to guarantee horizontal epipolar lines, however, it is necessary to set the optical axes of the two cameras in parallel.

Figure 2:
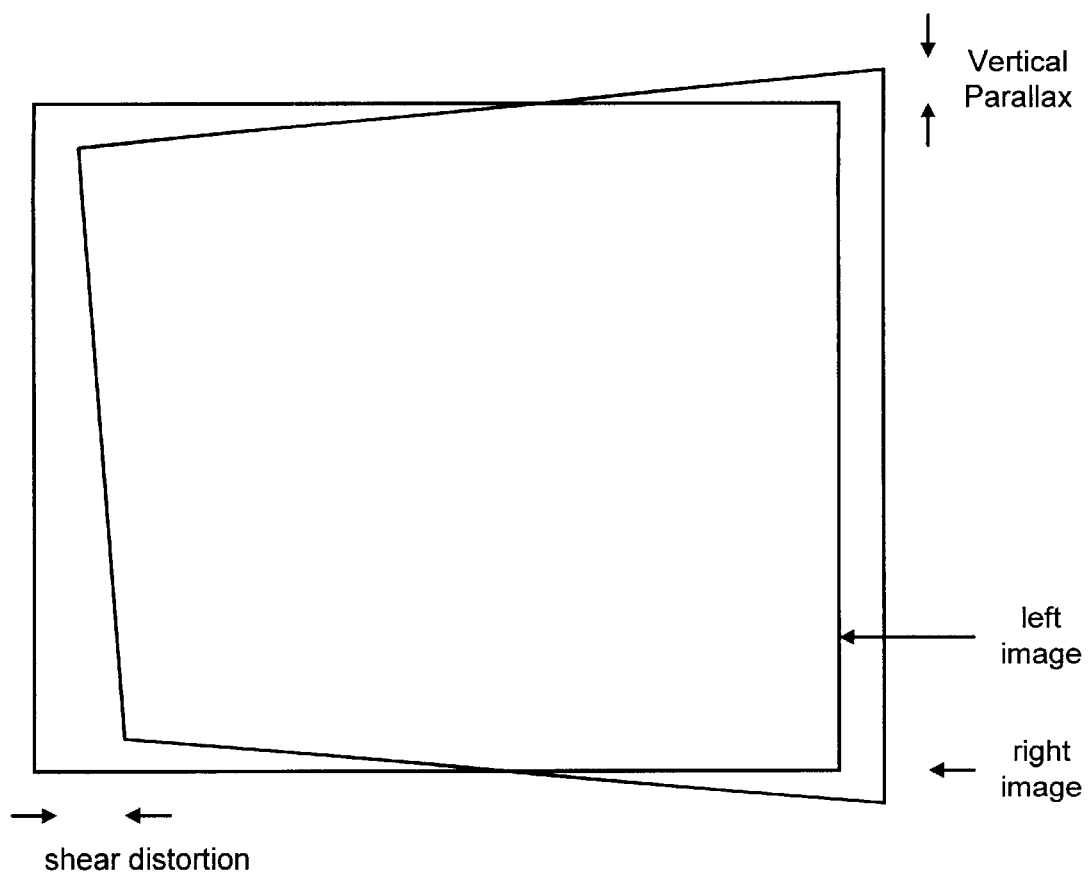
FIG. 2 is an illustration of stereoscopic (Keystone) distortions resulting from the geometry of the system of FIG. 1.

Matching points in one image 110 with points in another image 120 where both images are taken of a single scene, called the correspondence problem, remains one of the bottlenecks in computer vision and is important to continued development in this field. As will be more fully described below, the present invention adjusts the points in the second image 120 that correspond to the points in the first image 110, so that the points in the second image 120 are located along the same line as in the first image 110, thereby creating images with the desired epipolar geometry. In alternative embodiments, however, the first 110, second 120 or both images 110,120 may be adjusted. As soon the correspondence between points in two images is known, it is possible to recover the disparity field, which is the displacement of corresponding points along the epipolar lines in the two images, i.e. c and d parameters in equation 1, equation 2, and FIG. 2.

Figure 3:
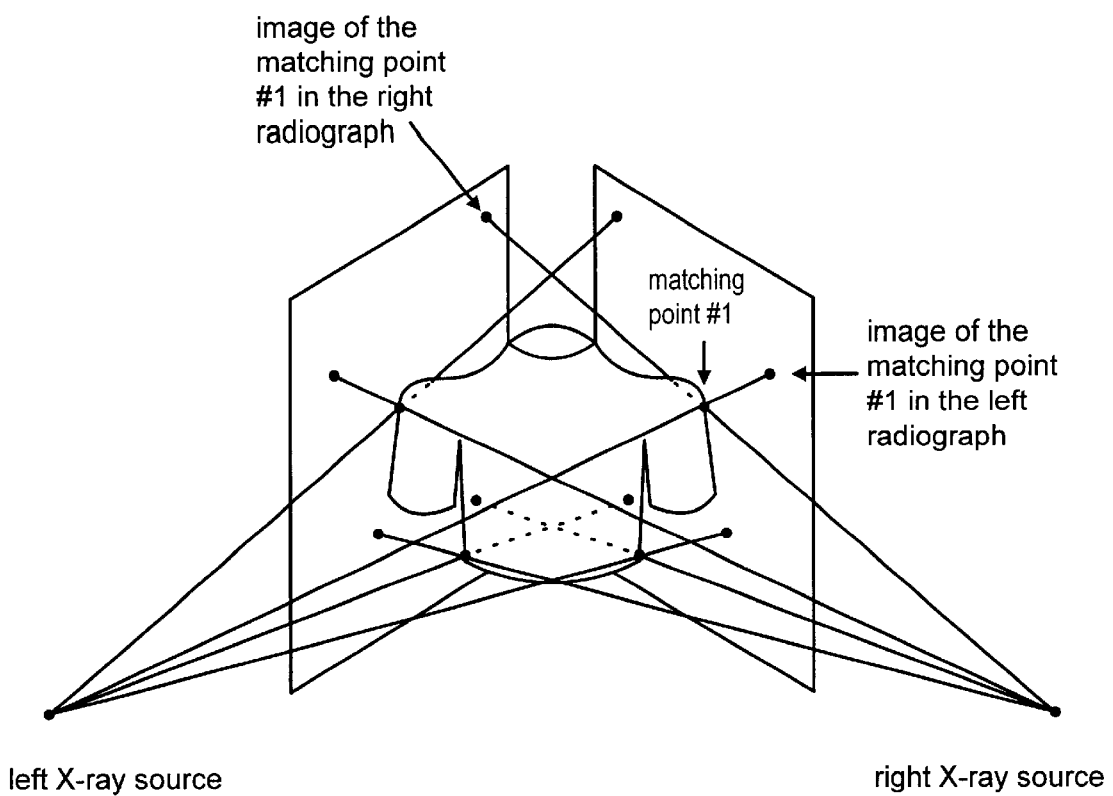
FIG. 3 is an illustration of a stereoscopic system for distortion correction in accordance with an embodiment of the present invention.

Referring now to FIG. 3, two or more distinct physical pointers are provided by or on or in a body being radiographed. For example, the physical pointers could be one or more small objects attached to the body such as special ink marks, small metal balls, foil stickers, or other items. The pointers may be artificially created or may exist naturally. Alternatively, the physical pointers need not even be attached to the body. For example, the pointers could be placed on poles near the body. In another alternative embodiment, the physical pointers could exist inside the body as distinct objects. The only constraint on the physical pointers is that the image of these pointers in the radiographs must have features that are distinguishable from other objects in and around the body and must be captured in the images.

The present invention can use a conventional C-arm digital radiograph system that rotates around the body in synch with a digital screen. The images of the matching points are shown in the left and right radiographs. Alternatively, the object itself may be rotated. In yet other embodiments, the images may be converted to digital images by scanning them. Once the image capture is complete, the previously placed physical pointers are located in the radiographs. If small steel balls were used, the balls will be represented by dark spots in each quarter of the image.

The physical pointers can be used as reference points to determine the vertical shift between the same matching points. One method for performing this task is described below with reference to FIG. 6. Alternatively, other transformation algorithms may be applied.

Horizontal adjustment of the radiographs is performed by placing the base line parallel to the screen and the screen perpendicular to the optical axis. The same technique described above could then be used to make horizontal adjustment of stereo pairs. In this case, the radiographs are adjusted such that the feature points are moved to the same rectangular positions.

Figure 4:
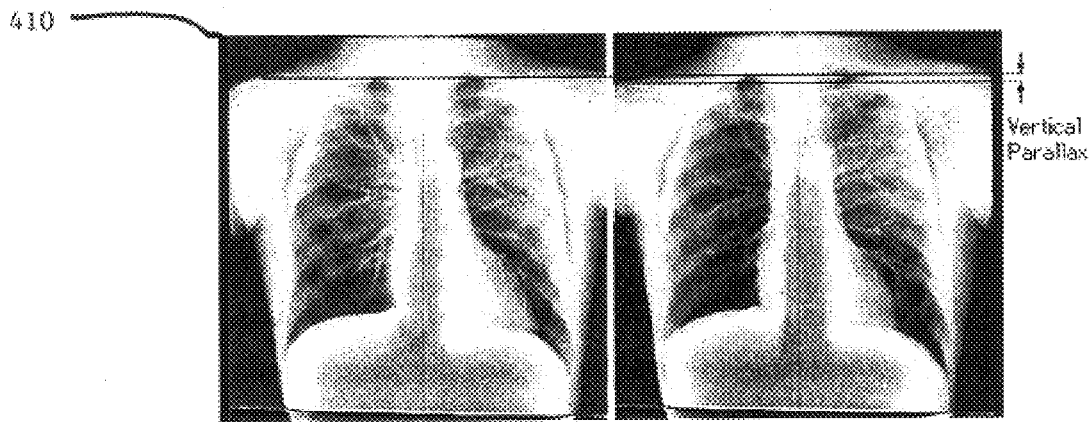
FIG. 4 is an illustration of distorted and corrected stereoscopic radiographs in accordance with an embodiment of the present invention.
Figure 4:
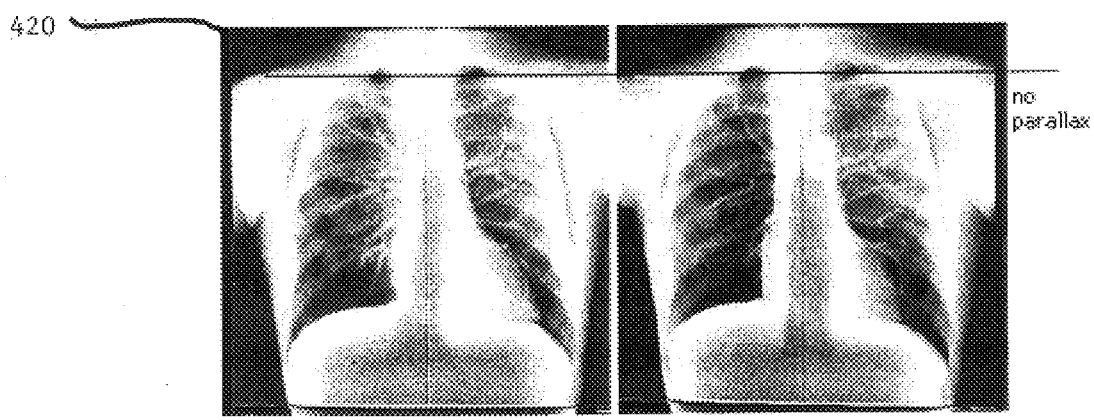

FIG. 4 shows stereo X-ray pair before 410 and after 420 vertical and horiontal adjustment. The feature points were determined manually and it can be seen that the vertical parallax evident in the first pair was eliminated after adjustment.

Figure 5:
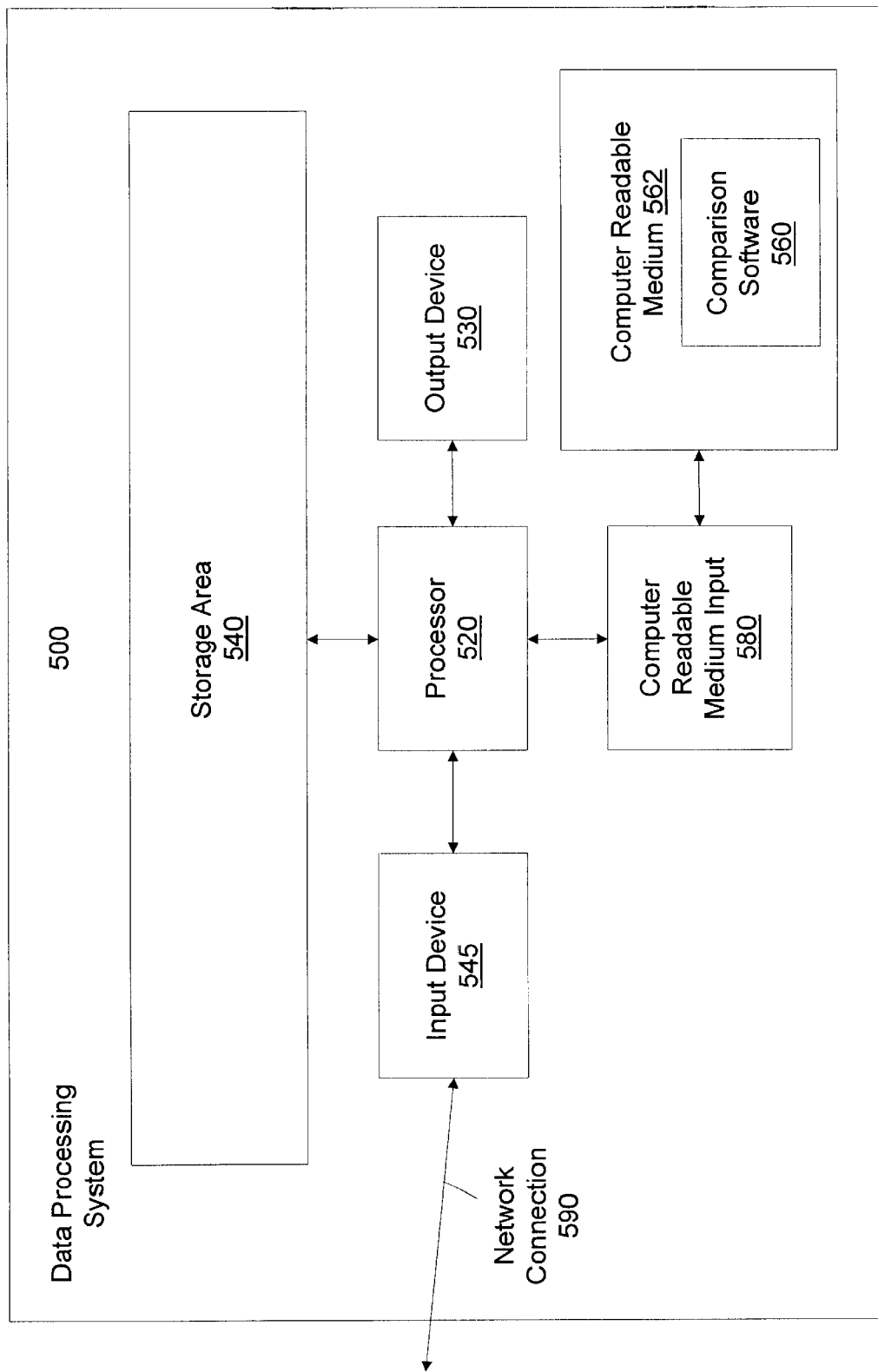
FIG. 5 is a block diagram of a data processing system in accordance with an embodiment of the present invention.

FIG. 5 is a block diagram of a data processing system 500 which has at least one processor 520 and storage 540. Storage 540 of system 500 includes one or more images, comparison software 560, and data structures used by the matching algorithm (not shown). The steps of the described embodiment of the present invention are performed when instructions of a computer program are performed by processor 520 (or another appropriate processor) executing instructions in storage 540.

System 500 also includes a network connection 590, which connects system 500 to a network such as the Internet, an intranet, a LAN, or a WAN. System 500 also includes an input device 545, such as a keyboard, touch-screen, mouse, or the like. System 500 also includes an output device 530 such as a printer, display screen, or the like. System 500 also includes a computer readable medium input device 580 and a computer readable medium 562. Computer readable medium 562 can be any appropriate medium that has instructions, such as those of comparison software 560 stored thereon. These interactions are loaded from computer readable medium 562 into storage area 540. Instructions can also be loaded into storage area 540 in the form of a carrier wave over network connection 590. Thus, the instructions and data in storage 540 can be loaded into storage via an input device 580, via a network, such as the internet, a LAN, or a WAN, or can be loaded from a computer readable medium such as a floppy disk, CD ROM, or other appropriate computer readable medium. The instructions can also be downloaded in the form of a carrier wave over a network connection.

System 500 also includes an operating system (not shown). A person of ordinary skill in the art will understand that the storage/memory also contains additional information, such as application programs, operating systems, data, etc., which are not shown in the Figure for the sake of clarity. It also will be understood that data processing system 500 (or any other data processing system described herein) can also include numerous elements not shown, such as additional data, software, and/or information in memory, disk drives, keyboards, display devices, network connections, additional memory, additional CPUS, LANS, input/output lines, etc.

Figure 6:
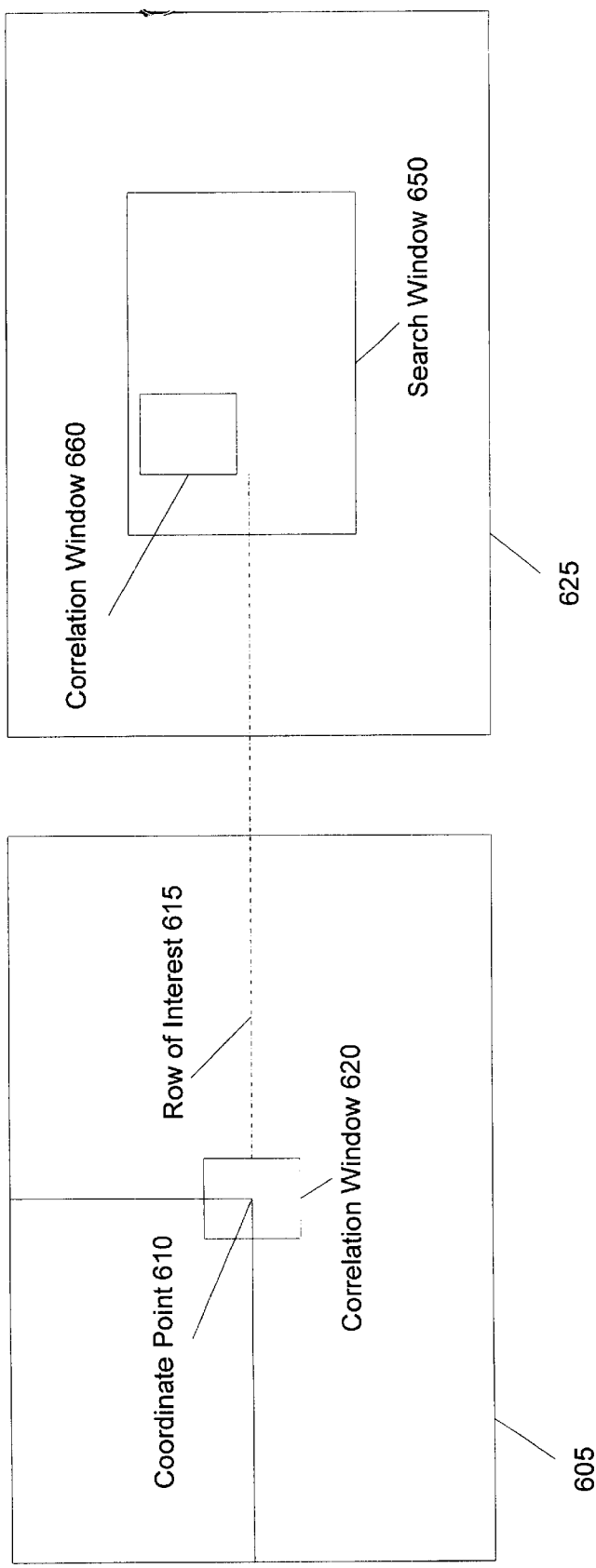
FIG. 6 is a sample image that illustrates a preferred method for establishing match candidates among points in the images.

Referring now to FIG. 6, a technique for establishing match candidates between two images is shown. For a given point 610 in the first image 605, a correlation window 620 centered at this point 610 is created. Once the point 610 has been selected in the first image 605, a search window 650 is selected in the second image 625. The size and location of the search window 650 may reflect some a priori knowledge about the disparities between the points in the images 605 and 625 if desired. If no such knowledge is available, the whole image may be searched.

Once the search window 650 has been selected, a correlation operation is performed. First, a correlation window 620 about the point 610 of interest in the first image is created. The correlation window 620 may be of any size, but a larger window 620 will yield less precise results. The value of one or more properties of the area within the correlation window 620 of the first image 605 are then determined. For example, the correlation operation may use the amount of red in the pixels within the correlation window 620 as the relevant correlation property.

A correlation window 660 is then centered around every point within the search window 650 in the second image 625. The value of one or more properties for areas within window 660 for every point is then determined. Each correlation window 660 for every point within the search window 650 in the second image 625 is given a correlation score based on its similarity to the properties of the correlation window 620 of the first image 605.

A constraint on the correlation score can then be applied in order to select the most consistent matches: for a given couple of points to be considered as a match candidate, the correlation score must be higher than a given threshold, for example. Using the correlation technique, a point in the first image may be paired to several points in the second image and vice versa. Several techniques exist for resolving the matching ambiguities but, for simplicity, the points with the highest correlation score are selected. While this method does provide a number of match candidates, there are no guarantees on the accuracy of the match. Assuming the threshold is set prior to processing, there is no guarantee that only the most precise matches will be used. Although this is the preferred technique for matching the points in the images, other matching techniques may also be used including correlation-based, MRF-based, feature- based and phase-based matching.

Although the description above contains many detailed descriptions, these descriptions should not be construed as limiting the scope of the invention but merely as providing illustrations of some of the presently preferred implementations of this invention. For example, although this method was described with reference to a standard rectangular image, this method can be used to correct images of any shape or size. Additionally, although the method was described with reference to external fiducials, internal regions and areas of the image may also be used to establish reference points. Thus the scope of the invention should be determined by the appended claims and their legal equivalents, rather than by examples given.

I claim:

1. A method for adjusting two two-dimensional x-rays taken of a body, the body having at least one object, the method comprising:

locating at least one physical pointer around the body;

capturing two distinct x-ray images of the body using an x-ray imaging device wherein the physical pointers are captured in the x-ray images;

estimating epipolar geometry and horizontal and vertical distortions using the location of the physical pointers in the images; and adjusting at least one image vertically and horizontally to correct for any estimated distortions.

2. The method of claim 1, further comprising the step of calculating a disparity map.

3. The method of claim 2, wherein the disparity map is calculated using a classic epipolar stereo matching technique.

4. The method of claim 1, further comprising the step of calculating the location of at least one object inside the body.

5. The method of claim 4, where e step of calculating the location of at least one object comprises using the equations $$x = \frac{da + db - dc}{b + d - c},$$

$$y = f\frac{d - c}{b + d + c},$$

where f is the focal length, b is the distance between the location of the x-ray imaging device when taking a first image and taking a second image, respectively, a is the X coordinate of the x-ray imaging device when capturing the first image, c is the X coordinate of the object in the first image, and d is the X coordinate of the object in the first image.

6. The method of claim 1, wherein at least one physical pointer comprises an ink mark.

7. The method of claim 1, wherein at least one physical pointer comprises a metal ball.

8. The method of claim 1, wherein at least one physical pointer comprises a foil sticker.

9. The method of claim 1 wherein the at least one physical pointer is located inside the body.

10. A method for adjusting two two-dimensional radiographs taken of a body, the body having at least one object, the method comprising:

locating at least one physical pointer around the body;

capturing two distinct radiographs of the body using a radiograph imaging device wherein the physical pointers are captured in the radiographic images;

estimating epipolar geometry and horizontal and vertical distortions using the location of the physical pointers in the images; and adjusting at least one image vertically and horizontally to correct for any estimated distortions.

11. The method of claim 10, wherein the at least one physical pointer is located inside the body.

12. A system for adjusting two two-dimensional x-rays taken of a body, the body having at least one object, the system comprising:

locating means for locating at least one physical pointer around the body;

capturing means, coupled to the locating means, for capturing two distinct x-ray images of the body using an x-ray imaging device wherein the physical pointers are captured in the x-ray images;

estimating means, coupled to the capturing means, for estimating epipolar geometry and horizontal and vertical distortions using the location of the physical pointers in the images; and adjusting means, coupled to the estimating means, for adjusting at least one image vertically and horizontally to correct for any estimated distortions.

* * * * *

UNITED STATES PATENT AND TRADEMARK OFFICE
CERTIFICATE OF CORRECTION

PATENT NO. : 6,381,302 B1  
DATED : April 30, 2002  
INVENTOR(S) : Alexander Berestov Page 1 of 1

It is certified that error appears in the above-identified patent and that said Letters Patent is hereby corrected as shown below:

<u>Column 3,</u>  
Line 40, "a" should read -- is a --; and  
Line 43, "first" should read -- second --.

<u>Column 6,</u>  
Line 52, "where e" should read -- wherein the --; and  
Line 66, "first" should read -- second --.

<u>Column 7,</u>  
Line 7, "claim 1" should read -- claim 1, --.

Signed and Sealed this

Second Day of December, 2003

JAMES E. ROGAN  
*Director of the United States Patent and Trademark Office*